US007893380B2

(12) United States Patent
Moore

(10) Patent No.: US 7,893,380 B2
(45) Date of Patent: Feb. 22, 2011

(54) ARC-EXTINGUISHING COMPOSITION AND ARTICLES MANUFACTURED THEREFROM

(75) Inventor: Jeffrey A. Moore, Lake Zurich, IL (US)

(73) Assignee: S&C Electric Company, Chicago, IL (US)

(*) Notice: Subject to any disclaimer, the term of this patent is extended or adjusted under 35 U.S.C. 154(b) by 0 days.

(21) Appl. No.: 11/969,651

(22) Filed: Jan. 4, 2008

(65) Prior Publication Data

US 2008/0169271 A1 Jul. 17, 2008

Related U.S. Application Data

(63) Continuation of application No. 10/887,937, filed on Jul. 9, 2004, now abandoned.

(51) Int. Cl.
*H01H 33/02* (2006.01)
*H01H 33/04* (2006.01)
*C07D 251/54* (2006.01)

(52) U.S. Cl. ...................................... 218/158; 544/200

(58) Field of Classification Search ..................... 252/5; 218/158
See application file for complete search history.

(56) References Cited

U.S. PATENT DOCUMENTS

| | | | | |
|---|---|---|---|---|
| 2,368,451 | A * | 1/1945 | D Alelio | 528/256 |
| 3,862,265 | A * | 1/1975 | Steinkamp et al. | 525/285 |
| 4,307,369 | A * | 12/1981 | Jackson, Jr. | 337/282 |
| 5,070,145 | A * | 12/1991 | Guerdoux | 525/179 |
| 5,422,418 | A * | 6/1995 | Maj et al. | 528/324 |
| 5,756,571 | A * | 5/1998 | Moore | 524/425 |
| 5,814,384 | A * | 9/1998 | Akkapeddi et al. | 428/35.7 |
| 2002/0156160 | A1* | 10/2002 | Martin | 524/101 |

OTHER PUBLICATIONS

Olabisi, O.; "Handbook of Thermoplastics", 1997, p. 650.*

* cited by examiner

*Primary Examiner*—Mark Eashoo
*Assistant Examiner*—Peter F Godenschwager

(57) ABSTRACT

An arc-interrupting compound, such as melamine, and to a method of extinguishing an arc by disposing the composition along the path of the arc, for contacting the arc. In one embodiment, the binder, or at least a portion of the binder, is a polymer that contains a functional group that binds to a coupling agent that is included in the arc-extinguishing composition. The coupling agent ties the polymeric binder to the arc-extinguishing compound, e.g., melamine, to provide new and unexpected physical strength and stability to the composition. In this embodiment, the molded composition, including the arc-interrupting compound coupled to the binder, maintains excellent arc-interrupting capability, while providing chemical stability and electrical insulating properties as well as unexpected physical strength.

34 Claims, 5 Drawing Sheets

ARC-EXTINGUISHING COMPOSITION AND ARTICLES MANUFACTURED THEREFROM

CROSS-REFERENCE TO RELATED APPLICATION

This application is a continuation of application Ser. No. 10/887,937, filed Jul. 9, 2004 now abandoned, the entire disclosure of which is incorporated herein by reference.

FIELD

The present invention relates to arc-quenching materials and articles fabricated therefrom for high-voltage electrical devices and equipment such as circuit interrupters wherein, under certain conditions of operation, a high-voltage electrical arc is produced that is either desirably, or by necessity, quenched. More particularly, the present invention relates to a composition to achieve arc-quenching and structural properties in devices such as circuit interrupters, high-voltage fuses, circuit breakers, and separable cable connectors.

BACKGROUND AND PRIOR ART

To provide effective circuit interruption in circuit interrupters, fuses, and the like, it is desirable to utilize an arc-quenching material or composition to quench and suppress arcing during electrical contact separation or fuse operation. Of necessity, the arc-quenching materials should include characteristics and properties sufficient for the particular application so as to be effective in quenching arcs via the rapid evolution of quenching gases. Of course, the evolved quenching gases should also be relatively nonconductive. In addition, it is also important that the arc-quenching materials are capable of being molded or otherwise fabricated into suitable articles and shapes having desirable structural properties, thermal stability, and environmental resistance to thermal cycling.

In many circuit-interrupting devices, it is typical to utilize a trailer/liner configuration, as well known in the art, so that the arc is drawn into an annular space defined between the trailer and the liner, each of which is preferably fabricated from an arc-quenching composition. The action of the gases produced by the trailer and/or liner on the confined arc tends to deionize the arc and force its extinction. Examples of trailer/liner configurations are shown in the following U.S. Pat. Nos. 2,351,826; 2,816,980; 2,816,978; 2,816,985; 4,103,129; and 3,909,570 and in Descriptive Bulletin 811-30 of S&C Electric Company, Chicago, Ill. Similarly, in high-voltage fuses, which also can be characterized as circuit interrupters, a sleeve or liner surrounds the path of the arc during fuse operation with the sleeve or liner being fabricated from an arc-extinguishing material. Reference may be made to U.S. Pat. Nos. 3,629,767 and 4,307,369 for an example of fuses of this type surrounded by arc-extinguishing sleeves or liners.

Typical arc-extinguishing materials and their properties are disclosed in the following U.S. Pat. Nos. 3,582,586; 4,251,699; and 4,444,671. One composition in U.S. Pat. No. 3,582,586 includes melamine and polyethylene. While this composition is generally suitable for various applications and exhibits desirable arc-quenching properties, for many applications, it would be desirable to achieve a composition with improved mechanical characteristics and environmental resistance to thermal cycling while maintaining the desirable arc-quenching characteristics.

One of the most effective arc-interrupting compounds used in this art for arc-quenching is melamine ($C_3N_6H_6$) which is a white crystalline powder having a melting point of about 350° F. and sublimes at its melting temperatures and below. Other, related nitrogen-containing compounds are also recognized in the prior art as arc-quenching or arc-interrupting compounds and are disclosed in Amundson et al U.S. Pat. No. 2,526,448. Melamine and its related compounds have excellent arc-interrupting characteristics but suffer from extreme structural weakness, so that they cannot be molded or pressed into satisfactory structural shapes except in combination with a suitable binder.

For a binder to be most effective in an arc-quenching or arc-interrupting composition it should volatilize or decompose in the presence of an electric arc, as does melamine. The binder, however, does not necessarily have to provide any arc-interrupting or arc-extinguishing characteristics to the composition, since, in some cases, the arc-interrupting characteristics of the melamine included in the composition is sufficient for arc-interrupting purposes. The binder, therefore, is primarily included for purposes of providing the melamine-containing composition with sufficient moldability and to provide a molded structure of sufficient physical strength, physical and chemical stability, and electrical insulating properties to provide a structurally sound, molded product. The physical strength of the molded product is most evident in its tensile strength, its percent elongation, and the amount of energy required to break the molded structure, or impact strength.

Structural damage, i.e., cracks have been found in prior art devices containing polyethylene as its primary binder material, and such damage is unacceptable in this art, since the break point allows another air space for the gases and arc to fill, thereby significantly lessening the arc-interrupting properties of the arc-interrupting device. Further, failed arc extinguishing compositions that contain melamine usually fail because the pressure wave associated with the arc causes the composition to physically break before it has an opportunity to extinguish the arc. The arc-extinguishing compositions described herein extinguish the arc without physically breaking. Thermoplastic polymeric binders have been found to be the most useful in arc-interrupting compositions based upon melamine or similar compounds, since the thermoplastic binders volatilize or decompose in the presence of an electric arc at lower power conditions than necessary to sublime melamine thereby producing large volumes of gas to drive the melamine into the core of the arc and to extinguish the arc under a wide range of power conditions. Further, the thermoplastic binders provide compositions with good molding characteristics, stability and electrical insulating properties.

Typical thermoplastic polymeric resins known to be useful as binders in melamine-based arc-interrupting compositions include polyethylene, polypropylene, polytetrafluoroethylene, acrylics, polystyrene, cellulosics polyamides (nylons), polyacetals (DELRIN), polyphenylene oxides, blends such as ABS, and polyimides. Other binders, such as thermosetting resins, epoxy resins, polyester resins, phenolic resins, and the like, also are known to be useful as binders in arc-interrupting compositions. It is also known to include elastomeric, rubber-like materials as a portion of the binder in melamine-based arc-interrupting compositions such as butyl compounds, isoprene-based compounds, neoprene-based compounds and other synthetic elastomers.

In this assignee's U.S. Pat. No. 4,975,551, there is disclosed a binder comprising a carboxylic acid group-containing polymer, particularly a copolymer of two different monomers, at least one of which contains a carboxylic acid moiety, such as an ethylene acrylic acid copolymer. As disclosed, the carboxylic acid functionalities of the binder interact with arc-extinguishing compounds having carboxylic acid-active sites, such as amine, thiol, alcohol, halogen, and the like sites, to provide added physical strength and stability to the composition. The molded composition, including the arc-interrupting compound and the binder, maintains excellent arc-interrupting capability, chemical stability and electrical insulating properties as well as increased physical strength.

SUMMARY

In brief the present invention is directed to a new and improved arc extinguishing composition including, a new and improved binder for compositions containing an arc-interrupting compound, such as melamine, and to a method of extinguishing an arc by disposing the composition along the path of the arc, for contacting the arc. In one embodiment, the binder, or at least a portion of the binder, is a polymer that contains a functional group that binds to a coupling agent that is included in the arc-extinguishing composition. The coupling agent, which may be a polymer that is compatible with the binder, contains a functional group that binds to the arc-extinguishing compound to tie the polymeric binder to the arc-extinguishing compound, e.g., melamine, to provide new and unexpected physical strength and stability to the composition. In this embodiment, the molded composition, including the arc-interrupting compound coupled to the binder, maintains excellent arc-interrupting capability, while providing chemical stability and electrical insulating properties as well as unexpected physical strength.

In other embodiments of the arc-extinguishing compositions and articles described herein, the melamine or other arc-extinguishing compound provides unexpectedly better results when incorporated into the composition in finely divided form; and improved results are provided by combining a plasticizer for the polymeric binder.

At least three embodiments of the arc-quenching materials and articles are described herein—each embodiment providing improved mechanical properties and/or arc-extinguishing results either alone or in combination with one or both of the other embodiments. Each of these three individual embodiments can be included alone in the materials and articles described herein or any two or three of these embodiments can be combined to further improve the materials and articles described herein.

In brief, the three embodiments are as follows:

(1) Incorporating a coupling agent into the arc-extinguishing composition that interacts mechanically and/or chemically with both the arc-extinguishing material and the polymeric binder to improve the mechanical properties and/or the arc-extinguishing properties of the composition and articles described herein.

(2) Incorporating a plasticizer for a base binder polymer (e.g., caprolactam for a nylon base polymer) into the arc-extinguishing composition to enhance elongation and other mechanical properties, especially reducing brittleness of the arc-extinguishing composition; and (3) Incorporating a finely divided arc-quenching material into the arc-extinguishing composition. Preferably, the arc-quenching material is selected from the group consisting of melamine, guanidine, guanidine acetate, guanidine carbonate, 1,3-diphenylguanidine, cyanurates, melamine cyanurates, hydantoin, allantoin, urea, urea phosphate, benzoguanamine, dithioammelide, ammeline, and a cyanuric halide, and/or derivatives and/or mixtures thereof. In accordance with this embodiment, the arc-quenching material should have a particle size distribution such that at least 90% by weight of the particles have a particle size less than about 200 μm, preferably less than about 150 μm, more preferably less than about 100 μm, and most preferably less that about 50 μm. To achieve the full advantage of this embodiment, at least 95% by weight of the arc-quenching particles having a particle size less than about 50 μm.

The arc-quenching compositions described herein are suitable for deionizing and extinguishing a high-voltage electrical arc. The compositions include effective amounts of an arc-extinguishing material, such as melamine, and sufficient binding polymer to achieve the desired combination of arc-extinguishing properties and structural characteristics, such as tensile strength, elongation, environmental resistance to thermal cycling, and the like. Additionally, the composition for various applications and uses may include additives, fillers or fibrous materials.

The composition is homogenized by compounding the constituents using dry blending, roll mill, extrusion and/or other plastic compounding techniques to obtain the molding resin compositions. The molding resin then is molded into articles of the desired shape using plastic processing techniques, such as injection molding, extrusion, and the like. In a preferred composition, for example, to form a trailer for an interrupter, a nylon base polymer binder is combined with melamine and an anhydride-functional coupling agent to achieve the desired arc-extinguishing and mechanical characteristics by virtue of the bonding and/or miscibility between the melamine, nylon, and the anhydride-functional coupling agent.

In other embodiments, as outlined above, the composition includes non-functionalized base polymeric binder(s) with or without the coupling agent and contains a finely divided arc-extinguishing material and/or a plasticizer for the base polymeric binder(s).

Accordingly, one aspect of the compositions, articles and methods described herein is to provide a new and improved arc-quenching composition comprising effective proportions of an arc-extinguishing compound, such as melamine, and a polymeric binder containing coupling agent-interactive moieties, such as an ethylene maleic anhydride polymer, and a suitable coupling agent capable of chemically and/or mechanically attaching the arc-extinguishing compound to the coupling agent and coupling the arc-extinguishing compound to the polymeric binder to achieve improved strength and desirable environmental resistance to thermal cycling.

Another aspect of the compositions, articles, and methods described herein is to provide a new and improved arc-extinguishing composition with improved mechanical characteristics, when molded, while exhibiting at least the same desirable electrical arc-extinguishing characteristics of previously available arc-extinguishing compositions and articles.

Another aspect of the compositions, articles and methods described herein, is to provide a new and improved arc-extinguishing composition including an arc-interrupting compound and a polymeric binder wherein the binder is a polymer, or copolymer formed from two different monomers, including coupling agent reactive groups or moieties for coupling the binder to the arc-interrupting compound through a coupling agent.

Another aspect of the compositions, articles and methods described herein, is to provide a new and improved arc-extinguishing composition including an arc-extinguishing compound having at least one site reactive with a coupling agent-contained functional group; or a polymeric binder material including a plurality of reactive coupling agent contained functional moieties, such that when the composition is molded under heat and pressure, the arc-extinguishing compound and the polymeric binder will chemically bond (including ionic and/or covalent bonds) to the coupling agent to provide new and unexpected physical strength in the molded composition.

Still another aspect of the compositions, articles and methods described herein, is to provide a new and improved arc-interrupting composition including an arc-interrupting compound having at least one reactive amine site in its molecule, such as melamine, and a thermoplastic resin binder material containing an amine-reactive site and a binder-reactive site; together with a suitable coupling agent for coupling the arc-interrupting compound to the polymeric binder through the coupling agent.

Another aspect of the compositions, articles and methods described herein, is to provide a new and improved arc-interrupting composition that provides sufficient and excellent arc-interrupting characteristics as well as new and unexpected molding and physical strength properties such as tensile strength, elongation and ability to withstand thermal cycling and resist cracking.

The above and other aspects and advantages of the present invention will become apparent from the following detailed description of the preferred embodiments, taken in conjunction with the drawings.

DETAILED DESCRIPTION OF THE PREFERRED EMBODIMENTS

Figure 1:
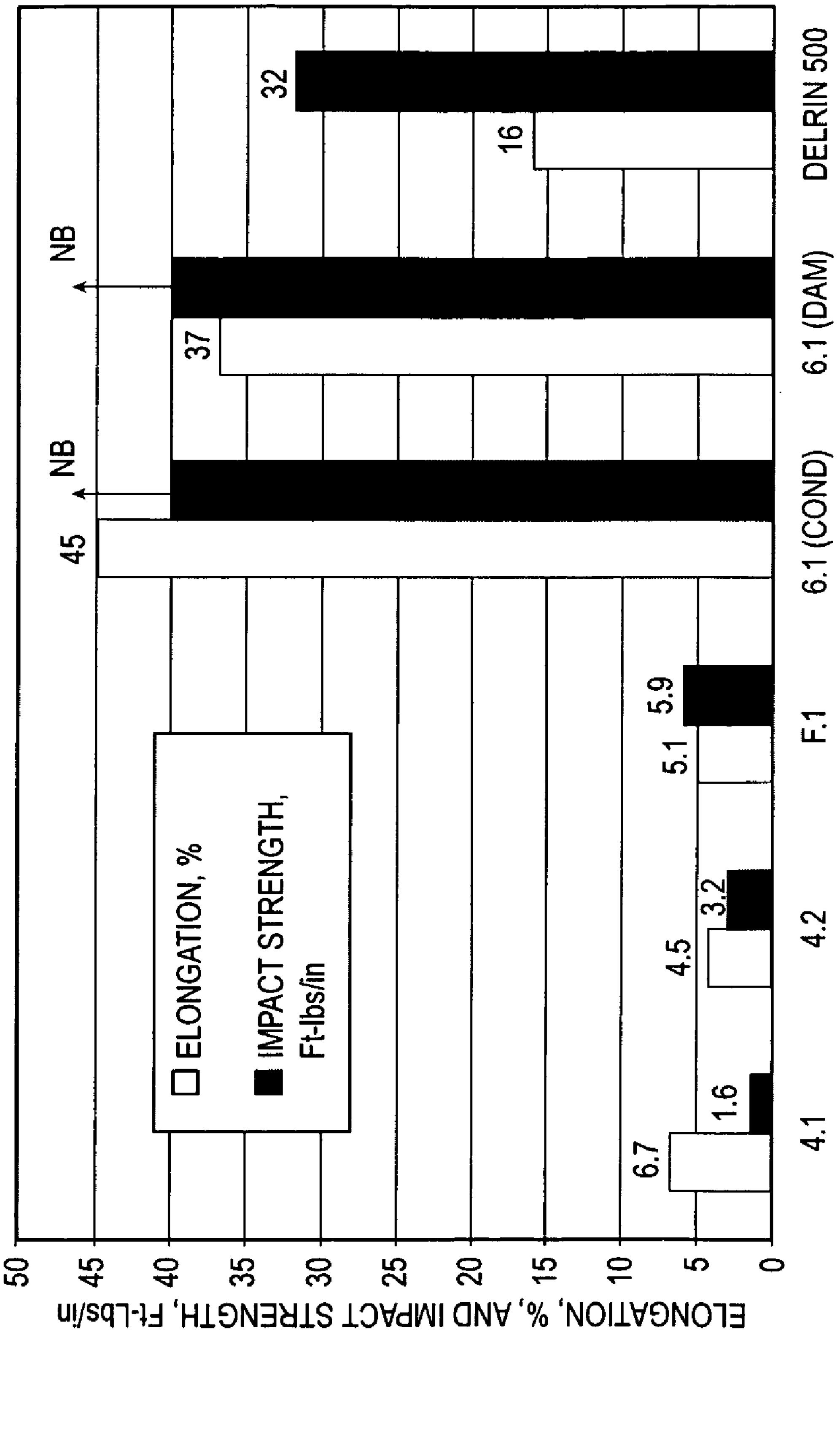
FIG. 1 is a bar graph showing mechanical toughness properties for the arc-extinguishing compositions of Table 1 in comparison to DELRIN 500.

In accordance with one embodiment of the compositions, articles, and methods described herein, it has been found that the physical and thermal properties of an arc-extinguishing composition can be unexpectedly improved when the arc-extinguishing composition includes a binder that contains a coupling agent-reactive functional group, such as an anhydride group, that bonds to coupling agent. These binders are particularly effective when used with arc-extinguishing compounds that have available reactive sites, such as amine groups; compounds containing one or more available hydroxyl groups, epoxy groups and/or aziridine groups; or compounds containing one or more available thiol groups having available carboxylic acid-reactive sulphur atoms, but are also effective with other arc-extinguishing compounds. The polymeric binders having one or more coupling agent-reactive functional groups, and the reactive coupling agents, described herein have been found to be particularly effective with melamine or other similar arc-extinguishing compounds, such as benzoguanamine, dithioammelide, ammeline, and a cyanuric halide.

The functionalized, coupling agent-reactive polymeric binder need not form 100% of the binder material used in the arc-extinguishing compositions and excellent results have been found in improvement of known arc-extinguishing compositions when the functionalized binder is included in only a small portion, e.g., 0.5 to 20% by weight, of the binder material used. The non-reacted (non-functional) portion of the coupling agent and polymeric binder should be sufficiently compatible such that the composition, when melted, forms a homogenous composition.

Suitable polymeric binders having one or more coupling agent-reactive functional groups include thermoplastic and thermosetting polymers having one or more functional groups selected from anhydride, carbonyl, hydroxyl, carboxyl, amine, amide, ether, lactam, lactone, epoxy, ester, sulfate, sulfonate, sulfinate, sulfamate, phosphate, phosphonate, and/or phosphinate; or an aromatic ring capable of covalently or ionically bonding to the coupling agent. Preferably, the binder has a functional group selected from anhydride, carbonyl, carboxyl, hydroxyl, amine, amide (particularly any nylon), ether, and/or an aromatic ring having a reactive group as part of the ring structure or as an extending coupling agent-reactive functional group. Examples of suitable polymeric binders containing these coupling agent-reactive functional groups include polypropylene, nylon 4/6, nylon 6/6, nylon 6, nylon 11, nylon 6/12, high-impact nylon, mineral-filled nylon, polycarbonate, polystyrene, acrylonitrile butadiene styrene, polysulfone, polybutylene terphthalate, polyethylene terphthalate, polyphenylene sulfide, polyester thermoplastic elastomer, polyetherimide, styrenic thermoplastic elastomer, olefinic thermoplastic elastomer, polyurethane thermoplastic, polyphenylene oxide, polyetheretherketone, phenylene ether co-polymer, polycarbonate/acrylonitrile butadiene styrene, polyarylether ketone, polyetherketoneetherketoneketone, polyphthalamide, and polyetherketoneketone and blends of any two or more of these polymers. Other suitable base resins include perfluoroalkoxy, ethylene tetrafluoroethylene, and polyvinylidene fluoride.

The functionalized binders used in one embodiment of the arc-interrupting compositions can be used in a widely varying amount, as well known in the art, together with the arc-interrupting or arc-extinguishing compound, such as melamine, and can be a combination of a number of different thermosetting and/or thermoplastic binder materials well known in the art. The functionalized binders are usually included in amounts of at least about 10% by weight of the total arc-interrupting composition and preferably in an amount of at least about 20% by weight of the arc-interrupting composition. The best results for purposes of molding, physical and chemical stability and strength, arc-interrupting characteristics and insulation properties are achieved when the total amount of functionalized binders are in the range of about 15% to about 50% by weight of the arc-interrupting composition, preferably in the range of about 20% to about 40%, based on the total weight of the finished molded arc-interrupting composition and article.

The coupling agents used in the coupling agent embodiment to tie the arc-extinguishing compound to the functionalized polymeric binder preferably is a monomeric or polymeric compound that contains reactive functional groups that provide covalent bonds to both the arc-extinguishing compound and the polymeric binder. However, the attractive interaction between the coupling agent and/or the arc-extinguishing compound and/or the polymeric binder also can be by any mechanism selected from the group consisting of electrostatic complexing, ionic complexing, chelation, hydrogen bonding, ion-dipole, dipole/dipole, Van Der Waals forces, and any combination thereof. The preferred coupling agent is a polymer, e.g., terpolymer, that has an anhydride functionality for reaction with the preferred melamine arc-extinguishing compound. For example, an ethylene/ethyl acrylate/maleic anhydride terpolymer coupling agent, e.g., Lotader 4720 from Atofina Chemicals Corporation, can react with a nitrogen atom of the melamine and a nitrogen atom of a nylon binder to couple the melamine to the nylon binder, e.g., nylon 6. The non-functional portion of the Lotader coupling agent is compatible with the nylon, e.g., nylon 6 polymeric binder. Other examples of suitable coupling agents include organosilanes, organofunctional silylating agents, particularly the organosilanes having an amino, epoxy, acrylate, n-mercapto and/or vinyl functionality including (3-Acryloxypropyl)trimethoxysilane; N-(2-Aminoethyl)-3-aminopropyltrimethoxysilane; 3-Aminopropyltriethoxysilane; 3-Aminopropyltrimethoxylsilane; 3-Isocyanatoproplytriethoxysilane; (3-Glycidoxypropyl)trimethoxysilane; 3-Mercaptopropyltrimethoxysilane; 3-Methacryloxypropyltrimethoxysilane; and Vinyltrimethoxysilane.

The preferred coupling agents are functionalized polyolefins, e.g., polyethylene or polypropylene that is functionalized with one or more reactive functionalities that provide reactivity or electrostatic association with the arc-extinguishing material and with the polymeric binder. The coupling agent preferably includes glycidylmethacrylate (GMA) and/or maleic anhydride (MAH) functional groups for better compatibility with polyester, polyamide and/or polyolefin polymeric binders. The most preferred coupling agents are functionalized polyolefins, particularly terpolymers of ethylene or propylene (PE or PP) with ethylacrylate (EA) and maleic anhydride (MAH) or glycidylmethacrylate having 6.5-30 wt. % EA; 0.3-3.1 wt. % MAH or GMA with the remaining 66.9 wt. % to 93.2 wt. % being PE or PP, preferably polyethylene. The terpolymer containing MAH is sold under the trade name Lotader, from Atofina Chemicals. Other suitable coupling agents include terpolymers of PE or PP with MAH and n-butyl acrylate (Lotader grades 2210, 3210, 4210 and 3410); MAH grafted ethylene/butane copolymers (elastomers), having about 0.25 wt. % to 1 wt. % MAH, sold by Dow Plastics, as AMPLIFY GR 208 functional polymers; titanate quarternary ammonium compounds, such as those sold by KENRICH petrochemicals as KEN-REACT® Water Soluble Chelate Titanate Quats and KEN-REACT® LICA®; KEN-REACT® NZ® Neoalkoxy Zirconates and Quats; KEN-REACT® KZ® Cycloheteroatom Zirconates; KEN-REACT® KA Reluminates; CAPOW® KR® and L® Series Titanate Coupling Agent Powders; styrene/maleic anhydride copolymers; epoxy modified polyolefins, particularly terpolymers of ethylene/methyl acrylate/glycidylmethacrylate (E-MA-GMA) or copolymers of ethylene and glycidylmethacrylate (E-GMA) having a GMA content of 3-8 wt. % and a methyl acrylate (MA) content of 0 or about 24-25% sold by Atofina Chemicals as Lotader AX8840; Lotader AX 8900 and Lotader AX8930; copolymers of ethylene and/or propylene with methacrylic acid (E/MAA) or (P/MAA), wherein the MAA acid groups have been partially neutralized, e.g., with metal, e.g., lithium, sodium or zinc, ions (DuPont SURLYN® 9320W); any Maleic Anhydride grafted polyolefin; any styrene/acrylonitrile grafted polyolefin; polypropylene/polymethylmethacrylate graft copolymers sold by Crompton Corporation as INTERLOY™ W1095H1; or the like.

The arc-interrupting compound included in the compositions described herein, such as melamine, is included in the compositions in their normal amounts, well-known in the art, and generally in amounts of about 5% to about 90% by total weight of the arc-interrupting composition, preferably about 10% to about 70%, more preferably about 20% to about 50%, based on the total weight of the composition. Excellent results are achieved with arc-interrupting compounds and binder materials present in proportions ranging from about four parts by weight of arc-interrupting compound to one part by weight of polymeric binder material by weight to about one part by weight of arc-interrupting compound to one part by weight of polymeric binder material. Best results are achieved when the arc-interrupting compound is included in the composition in an amount of two to three parts by weight of arc-interrupting compound per part by weight of polymeric binder material.

In the coupling agent embodiment described herein, of the total polymeric binder(s) included in the arc-interrupting composition, the functional group-containing polymers or copolymers should be included in an amount sufficient to improve the tensile strength of the molded composition, preferably more than a 10% increase in tensile strength, as a result of the addition of the functional group-containing binder.

For example, a typical prior art arc-interrupting composition includes melamine in a polyethylene binder in proportions of three parts by weight of melamine to one part by weight of polyethylene binder and has a tensile strength of 1133 psi. By replacing only 5% of the polyethylene with a coupling agent-interacting functionalized polymeric binder, such as ethylene/maleic anhydride, together with a suitable coupling agent for both the functionalized polymer and the melamine, the tensile strength is increased more than 10%. By totally eliminating the polyethylene and substituting 100% ethylene/maleic anhydride as the binder material for melamine, the tensile strength is increased to 1677 psi, or almost 50%. Physical strength improvements are achieved with the inclusion of the functional group-containing binder materials, and a coupling agent-reactive therewith, in binder amounts as low as about 0.5% based on the total weight of binders present in the composition up to 100% replacement of the binder material with the functional group-containing binder(s).

In the coupling agent embodiment described herein, to achieve the full advantage, the binder material used with the arc-interrupting compound should include the functional group-containing polymers or copolymers described herein in amounts of about 2% by weight to about 100% by weight preferably about 50% to about 100% by weight, based on the total weight of polymeric binders contained in the composition. The remaining percentage of binder material can be any binder effective for moldability and arc-extinguishing characteristics, such as the polyolefins, e.g. polyethylene and/or polypropylene; polyfluorinated resins, such as polytetrafluoroethylene, acrylic resins, polyamides, such as any nylon, and any other suitable binders, including thermosetting resins, such as epoxy resins, polyester resins, phenolic resins, and the like. Various elastomeric materials also may be included to improve the elongation properties of the molded compositions, such as butyl-based and/or isoprene-based and/or neoprene-based synthetic elastomers.

In the coupling agent embodiment described herein, the binders are useful with any arc-interrupting compound(s) to provide an arc-quenching composition that is readily moldable into a desired shape while exhibiting structural properties, thermal stability, and environmental resistance to thermal cycling heretofore impossible with known arc-quenching compositions. Very unexpected structural (mechanical) property improvements are achieved for the coupling agent embodiment when the arc-interrupting compound is a material that includes one or more reactive sites that are chemically reactive with one or more reactive moieties of a coupling agent, which is also chemically reactive with the functional binders described herein. For example, melamine ($C_6N_6H_6$) includes three equally spaced reactive primary amine moieties that can chemically bond (including ionic and/or covalent bonds) with the extending functional moieties of a vinyl/maleic anhydride binder, wherein the anhydride group acts as a coupling agent for the melamine, thereby achieving new and unexpected tensile strength, elongation and resistance to thermal cycling, while maintaining excellent arc-extinguishing properties.

In the preferred embodiment, the percentage of functional group-containing monomer used in forming a functionalized binder polymer or copolymer, such as in the copolymerization of ethylene with maleic anhydride, and the like, can be varied widely to provide sufficient reactive, e.g., anhydride moieties, in the copolymer for chemical bonding (including ionic and/or covalent bonds) at one, two or all three of the reactive amine sites extending from the melamine vinyl structure. In this manner, different degrees of compound-binder chemical bonding can be provided for different properties when the functional group-containing polymers are used as at least a portion of the binder in the manufacture of arc-quenching compositions.

In the coupling agent embodiment described herein, generally, the amount of functional group-containing monomer that should be polymerized, or copolymerized with a second monomer in forming copolymers, is from about 0.5 percent to about 80%, based on the total weight of the polymerizable monomers, with the second monomer present in an amount of about 20% by weight to about 95% by weight based on the total weight of both monomers. Such copolymers are readily available, such as the ethylene/maleic anhydride copolymers manufactured by Atofina containing various amounts of maleic anhydride monomer. The copolymer coupling agent sold by Atofina under the Trademark LOTADER 4720, provides an arc-quenching composition having exceptionally good structural characteristics, thermal stability and environmental resistance to thermal cycling. Other functionalized polymers and copolymers can be used having more or less coupling agent-reactive moieties, e.g., an anhydride percentage, and should provide similar structural improvements when used as a coupled binder in arc-quenching compositions.

In the coupling agent embodiment described herein, it is theorized that a reactive site on the arc-quenching compound chemically bonds (ionically and/or covalently) with the functional moiety of the polymeric binder to achieve new and unexpected tensile strength, elongation and resistance to cracking heretofore unachieved in the prior art. In addition to the reactive amine groups extending from melamine arc-quenching compounds, other arc-quenching compounds also include reactive sites, such as benzoguanamine having a pair of extending reactive amine groups; thio substituted organic arc-quenching compounds, such as dithioammelide; ammeline; and halogenated compounds such as cyanuric chloride. Each of these compounds has the ability to generate large volumes of arc-extinguishing gases under the influence of an electric arc. Each of these compounds is useful in accordance with compositions, materials, and articles described herein, in combination with the coupling agent-reactive binders; and/or finely divided form of the arc-extinguishing compounds; and/or the plasticizers for the polymeric binders, to achieve new and unexpected structural, mechanical and physical properties in an arc-extinguishing or arc-interrupting composition.

In accordance with the coupling agent embodiment described herein, it is theorized that a reactive, arc-extinguishing compound, such as melamine, undergoes chemical bonds (ionic and/or covalent bonding) with the functionalized polymeric binders described herein by reacting with the reactive functional group at one or more of the reactive compound sites.

Similarly, any arc-extinguishing compounds that have reactive epoxy groups, aziridine groups, thiol groups, hydroxyl groups, halogen groups, and like-reactive sites, also can chemically bond (including ionic and/or covalent bonds) with the reactive functional groups from the polymeric binders used in the compositions described herein to provide new and unexpected structural properties, thermal stability, and thermal cycling resistance.

The molecular weights of the reactive, functionalized polymeric binders vary widely and can range from a low of about 250 weight average molecular weight to a high of about 500,000 or more while achieving exceptionally good physical properties, thermal stability and resistance to thermal cycling in accordance with the compositions, articles, and methods described herein. It is preferred that the weight average molecular weight of the polymeric binders be in the range of about 1,000 to about 100,000 weight average molecular weight, and more preferably in the range of about 1,000 to about 50,000 weight average molecular weight.

Other materials may be added to the compositions and articles described herein for additional insulating, strength, and/or arc-extinguishing properties, generally in amounts of about 0.1% to about 10% each, based on the total weight of the composition. Fibrous additives include glass, inorganic fibers and organic fibers, such as polyacrylonitrile, polyamide and polyester fibers. Fillers that may be included are, for example, cellulosic materials, calcium carbonate, metal oxides, comminuted polymers, carbon black, and natural and synthetic silica materials.

Figure 6:
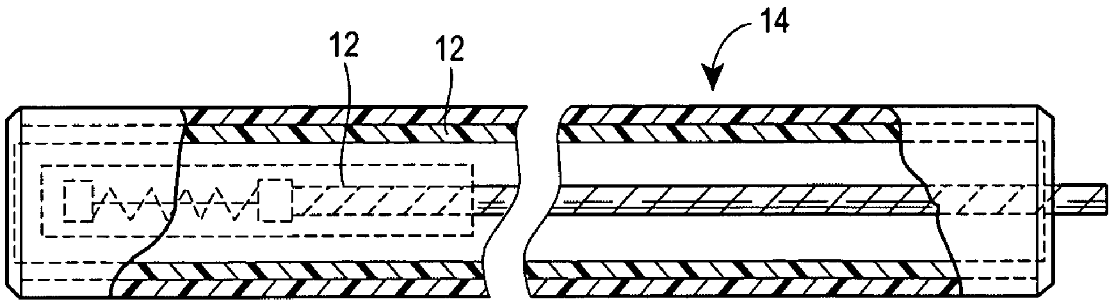
FIG. 6 is a partially broken-away side view showing the sleeve or liner of FIG. 1 surrounding a fuse.

FIG. 6 shows one example of a specific use of the arc-extinguishing materials in the form of molded or extruded annular fuse sheath or liner 10, manufactured (molded or extruded) from the arc-extinguishing compositions described herein, that is dimensioned to surround a fuse 12 disposed within a fuse tube 14. Such fuses 12 may be provided to interrupt both low and high level fault currents. At low fault currents, if the sheath 10 does not burst or rupture and remains integral, the arc between terminals is elongated entirely within the fuse tube 14. The elongating arc interacts with the arc-extinguishing material of the sheath 10, evolving arc-extinguishing gases. If sufficient arc-extinguishing gas is evolved from the sheath and if the pressure of this gas within the sheath remains sufficiently high at a current zero, there will be sufficient dielectric strength due to the presence of the arc-extinguishing gas to prevent reignition of the arc. The fuse 12 may also be called upon to interrupt high fault currents. At high fault currents the sheath usually ruptures and the extinguishment of the arc formed and elongated between terminals of the fuse is primarily due to the evolution of the arc-extinguishing gas from the bore of the fuse tube 14.

Data

In order to show the unexpected structural properties that are achieved with the embodiments described and claimed herein, as compared to other arc-extinguishing compositions, various compositions were prepared and tested, as shown in Tables 1-7.

TABLE 1

ARC-extinguishing-EXTINGUISHING COMPOSITIONS
Toughness Numbers

| Material/Toughness Measurement | Elongation, % | Unnotched Izod Impact Strength, ft-lbs/in |
|---|---|---|
| Delrin | 15-30 | 24-40 |
| X-Material* | 0.55 | 0.25 |

TABLE 1-continued

| ARC-extinguishing-EXTINGUISHING COMPOSITIONS Toughness Numbers | | |
|---|---|---|
| Material/Toughness Measurement | Elongation, % | Unnotched Izod Impact Strength, ft-lbs/in |
| TX-Material** | 3.9 | 3.2 |
| 70% Nylon/30% Melamine | 2.9 | 2.8 |

*70% melamine/30% nylon
**72% melamine/28% EAA

TABLE 2

| Material | %, Type Nylon 6 | %/Type Melamine | % Coupling Agent |
|---|---|---|---|
| 6.1 | 50 (note 1) | 30, Fine | 20 (3) |
| 6.2 | 50 (note 1) | 30, regular | 20 (3) |
| 6.6 | 50 (note 2) | 30, regular | 20 (3) |

Notes:
(1) This nylon 6 was impact modified, and plasticized with 4-8% Caprolactam (the monomer used to make Nylon 6)
(2) This nylon 6 was impact modified, no plasticizer.
(3) The coupling agent was Lotader 4720 (Atofina), 30% Ethyl Acrylate, 0.3% maleic Anhydride (Functional group), balance Ethylene.
(4) Both materials 6.1 and 6.2 had a rubber-like feel to them. Material 6.6 was less rubbery, and had more stiffness (increased modulus). From this data it is clear that the caprolactam is an effective material in imparting toughness (6.2 vs. 6.6) and the fine melamine also improved toughness (6.1 vs. 6.2). However, the biggest effect is from the coupling agent/impact modifier. The increase in toughness is dramatically better than that seen going from X-Material to TX-Material. It is also clear a family of materials with a balance of toughness and stiffness can be made.
(5) 6.1 material also proved to be a better AEM than Delrin, and to be more resistant to ozone and nitric acid. In addition, it can handle higher temperatures than X or TX.

For the electrical tests, samples were molded into arc compressor parts and slat-shaped parts. Results of the molding runs appear in the following data. These parts were then assembled in Arc Compressor Assemblies, using production parts to complete the assemblies.

Test Procedures

Three types of tests were performed: Mechanical, Environmental, and Electrical.

Mechanical Tests:

Tensile testing was performed per ASTM D 638. Elongation was estimated from crosshead movement. Unnotched Izod impact testing was performed per ASTM D 4812. Since the Nylon 6 is hygroscopic, samples were tested in both the conditioned, and dry as molded (DAM) state. The results for Delrin 500 from a previous experiment were used for comparison.

Environmental Test:

The environmental test consisted of immersing flex bars of material (½" by ⅛" by 5" long) most of the way into a solution of 10% Nitric Acid in DI water (by volume) for 7 days. Due to a miscalculation, the first 3 days were in a 7% solution. By not immersing the samples completely, an air/solution interface is created that tends to accelerate the chemical attack. Since Nylon 6 is hygroscopic, a control in 100% DI water was also run. The effect on weight and width was documented.

Electrical Test:

Electrical tests were run. In the first, the interruption test, the High Power Lab set up provided a nominal 25 kV, 400 A circuit. A travel record and timing shot were first done, then the switch was opened and closed, with arcing times on opening and pre-strike times on closing recorded.

For this testing, the samples were placed into a Mini-Rupter switch. A steel (unpainted) ground plane was placed in front of the Mini-Rupter, 8 inches from the tip of the Mini-Rupter blade when in the open condition. The Mini-Rupter strut was energized, and the ground plane, frame, and adjacent phases were grounded. No barrier boards were used anywhere in the switch. The results are shown in the graph of FIG. 1. Composition 6.1 was the first AEM material tested that matched or exceeded the toughness numbers for Delrin. Composition 6.1 also displayed rubber-like properties.

Figure 2:
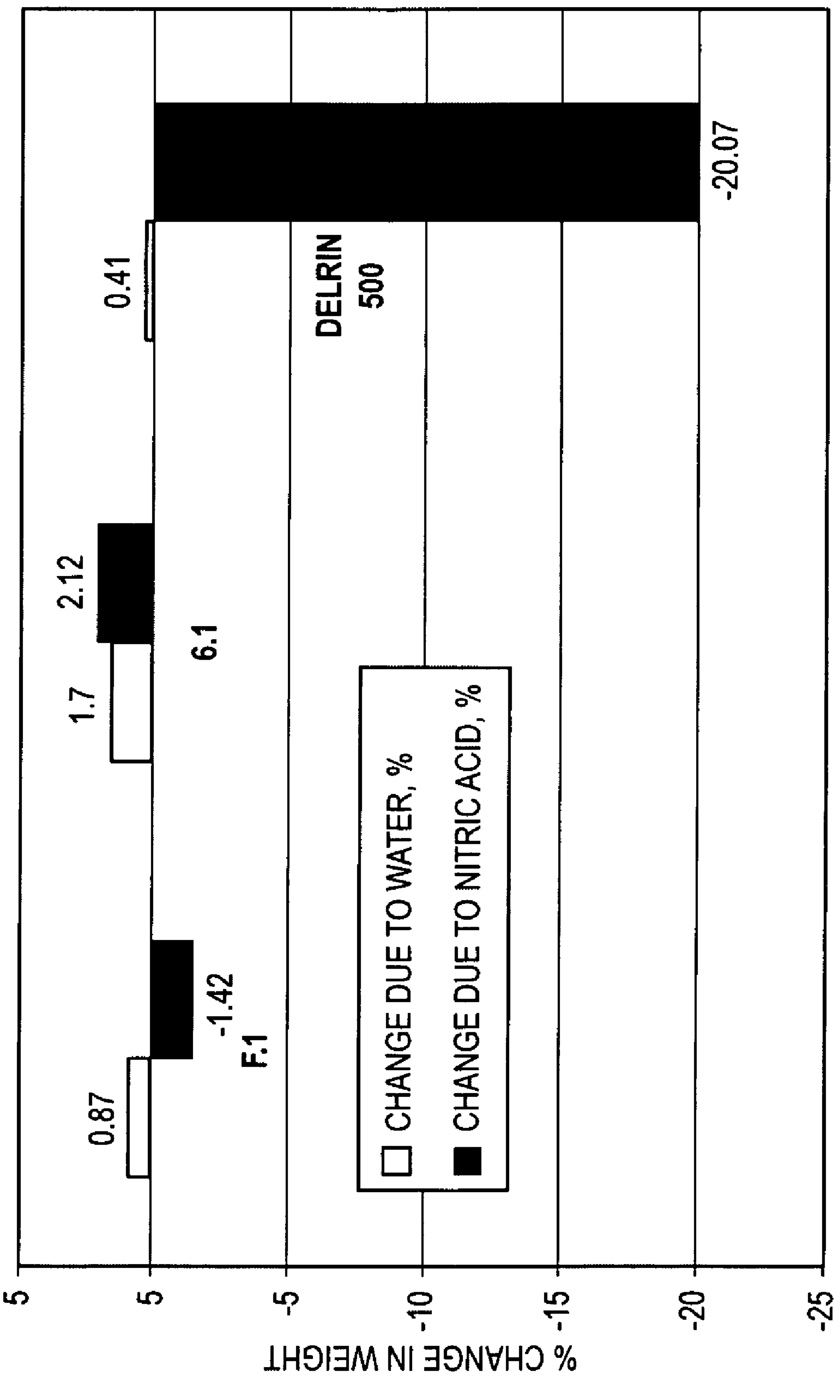
FIGS. 2 and 3 are bar graphs showing weight changes due to water and nitric acid attack on the arc-extinguishing compositions of Table 1 in comparison to DELRIN 500.
Figure 3:
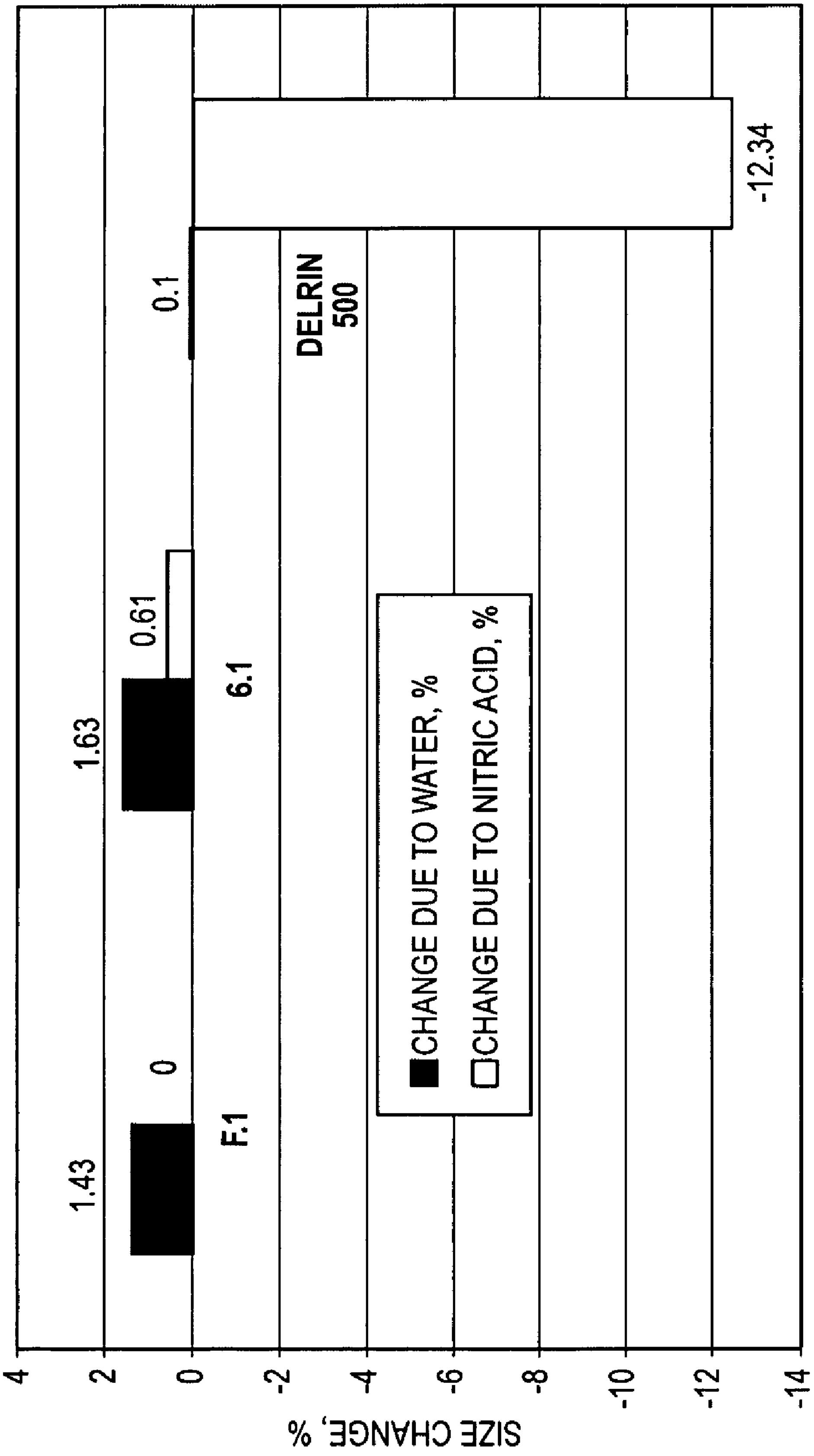

Environmental Tests:

The results of the environmental test appear in FIG. 2 (Weight Change) and FIG. 3 (Size Change). A positive change indicates a weight or size gain, a negative indicates a weight or size loss.

Both the 6.1 and the F.1 compositions provided much better resistance to nitric acid than the Delrin. They suffer surface attack in the form of yellowing, but no significant material loss. The Delrin sample showed severe erosion at the waterline, looking much like Delrin samples from the Swamp.

Note that the Nylon 6 material both gained 1.6% in weight and 1.6% in size due to water absorption.

Electrical Tests:

The results of the testing at 25 kV, 400 A (nominal) testing for composition 6.1 appears in Table 3. The arcing times for the 6.1 material was surprisingly better than the acetal control material (DELRIN). In the tests that involved restrikes for material 6.1, these restrikes were due to the compressors being too flexible, and allowing some hot gases to escape.

TABLE 3

| Compressors, Electrical Results, 25 kV, 400 A. | | | | | | |
|---|---|---|---|---|---|---|
| Trace # | Voltage, kV | Current, A | Closing Pre-Strike, ms | Opening Arc Time, ms | Video, ID | Notes |
| 29 | 24.6 | 382 | 3.6 | | | 6.1 |
| 30 | 24.2 | 381 | | 14 | | |
| 31 | 24.5 | 389 | 3.4 | | | |
| 32 | 24.4 | 375 | | 19 | | |
| 33 | 24.7 | 387 | 1.5 | | | |
| 34 | 24.9 | 383 | | 13.2 | 9 | |
| 35 | 25.6 | 400 | 4.9 | | 10 | |
| 36 | 24.8 | 378 | | 13.9 | 11 | |
| 37 | 25.4 | 392 | 2.1 | | 12 | |
| 38 | 24.6 | 385 | | 13.5 | 13 | |
| 39 | 24.5 | 399 | 1 | | 14 | |
| 40 | 24.9 | 383 | | 16.8 | 15 | Restrike, clear |
| n/a | n/a | n/a | n/a | | | No data |
| 44 | n/a | 382 | | 12.8 | 17 | Restrike, no clear |

TABLE 4

| Material | Elongation, % | Unnotched Izod Impact Strength, ft-lbs/in | Modulus (ksi) |
|---|---|---|---|
| 70% Nylon/30% Melamine (control) | 2.9 | 2.8 | na |
| TX-Material (Control) | 3.9 | 3.2 | na |
| 6.1 | 36.7 | No Break(1) | 50 |
| 6.2 | 20.5 | No Break(1) | 60 |
| 6.6 | 9.46 | No Break(1) | 137 |

Note
(1)material folds under blade without breaking.

Both materials 6.1 and 6.2 had a rubber like feel to them. Material 6.6 was less rubbery, and had more stiffness (increased modulus). From this data it is clear that the caprolactam is an effective material in imparting toughness (6.2 vs. 6.6) and the fine melamine also improved toughness (6.1 vs. 6.2). However, the biggest effect is from the coupling agent/impact modifier. The increase in toughness is dramatically better than that seen going from X-Material to TX-Material. It is also clear a family of materials with a balance of toughness and stiffness can be made.

6.1 material also proved to be a better AEM than Delrin, and to be more resistant to ozone and nitric acid. In addition, it can handle higher temperatures than X or TX.

TABLE 5

| AEM Weight Change | | |
|---|---|---|
| Material | Change Due to Water, % | Change Due To Nitric, % |
| F.1 (melamine with acrylic binder) | 0.87 | −0.42 |
| 6.1 | 1.70 | 2.12 |
| Delrin 500 | 0.41 | −20.07 |

TABLE 6

| AEM Size Change | | |
|---|---|---|
| Material | Change Due to Water, % | Change Due To Nitric, % |
| F.1 (melamine with acrylic binder) | 1.43 | 0.00 |
| 6.1 | 1.63 | 0.61 |
| Delrin 500 | 0.10 | −12.34 |

In accordance with a second embodiment of the arc-extinguishing compositions, articles and methods described herein, it has been found that when the arc-extinguishing compound is provided in finely divided form (see Table 2 and FIG. 4), the molded arc-extinguishing composition has unexpectedly increased toughness, and especially elongation, thereby preventing breakage of the molded articles.

In accordance with the second embodiment, wherein the arc-extinguishing compound is provided in finely divided form, it has been found that the compound should have a particle size distribution such that at least 90% by weight, up to 100%, of the particles have a size less than about 200 microns (μm). Preferably, at least 90% by weight of the particles have a particle size less than about 100 μm and, more preferably, at least 99% by weight of the arc-extinguishing compound particles have a particle size less than 100 μm. To achieve the full advantage of this second embodiment of the compositions, articles and methods described herein, at least 90% by weight, up to 100% by weight, of the arc-extinguishing compound particles should have a particle size less than 50 μm. Excellent increases in elongation of molded arc-extinguishing devices have been achieved with a finely divided melamine obtained from DSM, sold for other purposes, as Melamine Grade 003 having a particle size distribution as follows: 99 wt. % below 40 μm; 90 wt. % below 30 μm; 50 wt. % below 15 μm; and 10 wt. % below 5 μm.

In accordance with a third embodiment of the compositions, articles and methods described herein, it has been found that by including a plasticizer for the binder polymer into the compositions, the structural properties of the molded articles are increased without sacrificing arc-extinguishing properties.

To determine which plasticizer(s) is suitable for a particular polymer binder, compatible plasticizers should have a solubility parameter (δ) suitable for the particular polymeric binder, as well known in the art. One method of determining solubility parameters (δ) is in accordance with ASTM Designation D-3132-84 (Re-approved 1990). The plasticizer for the polymeric binders should have a solubility parameter (δ) as close as possible to the solubility parameter of the polymeric binder. For example, some of the preferred polyamide (nylon) polymeric binders have solubility parameters (δ) as follows:

| δ for binder | Preferred δ for plasticizer | δ for ϵ-caprolactam |
|---|---|---|
| Nylon 6: δ = 12.83 | 11.5-14.0 | 12.7 |
| Nylon 8: δ = 12.7 | 11.5-14.0 | |
| Nylon 11: δ = 11.065 | 10-13 | |
| Nylon 12: δ = 10.72 | 9-13 | |
| Nylon 6/6: δ = 12.95-13.6 | 11.5-14.0 | |
| Nylon 6/10: δ = 11.86 | 11-14 | |

Polyester polymeric binders have solubility parameters δ in the range of about 9.5 to 12. Maleic Anhydride has a δ of about 13.6. The adipate plasticizers have relatively low solubility parameters, but are suitable for plasticizing amines. Epoxys have δ s of about 9-11 and ethers have δ s of about 7.5-11. Ketones have δ s of about 8.4-10; lactones of about 10-14; maleates about 8.5-10; phenols about 9.5-13; phosphates about 7.5-10; phosphonates about 8-10. The above are general guidelines, and the solubility parameters for polymers (polymeric binders) and compatible solvents (plasticizers) for the polymeric binders are available, for example, in *Specific Interactions and the Miscibility of Polymer Blends: Practical Guides for Predicting & Designing Miscible Polymer Mixtures*, Michael M. Coleman, et al., Lancaster, Pa., U.S.A.; Technomic Pub. Co., c1991; and in C. M. Hansen, *J. Paint Technol.,* 1967. 39. 104.

In general, any of the monomers used to form a polymeric binder can be used as a plasticizer for that polymer binder (e.g., ϵ-caprolactam used to plasticize nylon 6) in accordance with the third (plasticizer) embodiment described herein. The plasticizer need only be compatible with the polymeric binder such that a homogeneous mixture is achieved when the arc-extinguishing composition is melted during the article molding process. If the plasticizer is not sufficiently compatible with the polymeric binder, the plasticizer will separate from the binder when melted, or will not form a homogeneous composition when melted together with the arc-extinguishing compound and other components of the composition.

Figure 4:
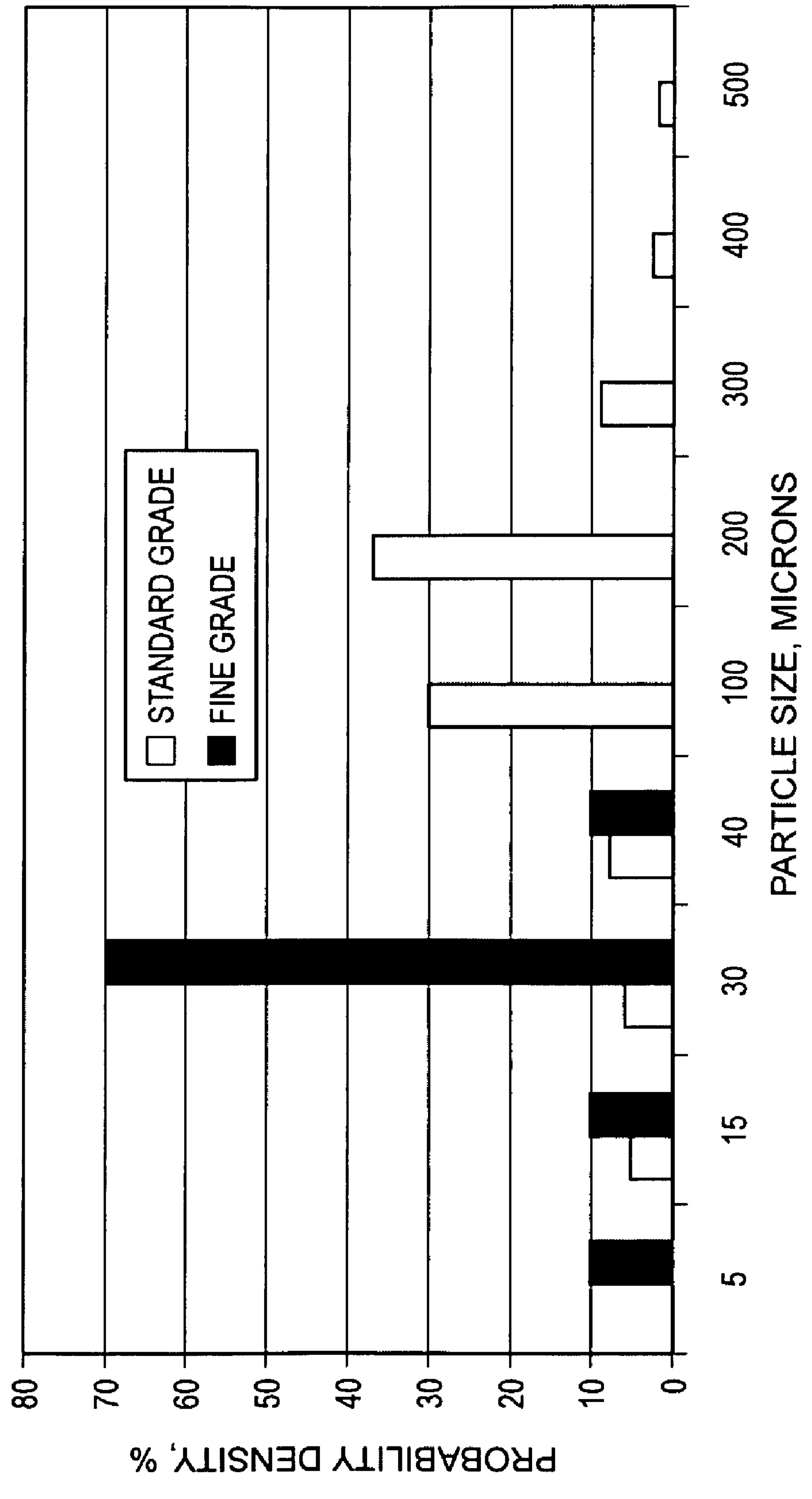
FIG. 4 is a bar graph showing the particle size distribution of standard grade and fine grade melamine.
Figure 5:
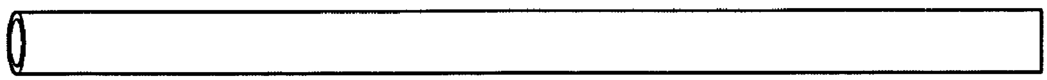
FIG. 5 is a perspective view of a fuse sleeve or liner formed from the arc-extinguishing compositions described herein.

The data of Table 7 compares the percent elongation achieved in molded articles containing DSM Melamine Grade 003 in comparison to the standard grade melamine. Compositions with and without a plasticizer also are shown in Table 7. A comparison of the finely divided melamine versus standard grade melamine is shown in FIG. 4.

As shown in Table 7, in comparison to control AEM-containing compositions containing (1) 70% nylon/30% melamine and (2) one of the materials of this assignee's U.S. Pat. No. 4,975,551 containing 72% melamine/28% ethylene acrylic acid (EAA), the compositions containing a reactive-functionality containing polymer binder (an ethylene/maleic anhydride copolymer) and a coupling agent for the reactive binder (LOTADER 4720-30% ethyle acrylate/0.3% maleic anhydride/69.7% ethylene copolymer).

The invention claimed is:

1. A method of extinguishing an electrical arc comprising:

encircling a fuse with a sheath or liner, the sheath or liner comprising an effective amount of an arc-extinguishing compound; a polymeric binder for the arc-extinguishing compound; and a polymeric coupling agent that binds the arc-extinguishing compound to the polymeric binder in an amount of about 2% to about 100% by weight based on the total weight of polymeric binder and polymeric coupling agent, and wherein the polymeric binder has a weight average molecular weight of at least 1,000 daltons; and positioning the sheath or liner such that if an arc forms within the sheath or liner, the sheath or liner evolves arc-extinguishing gasses, and the arc-extinguishing gases extinguish the arc.

2. The method of claim 1, wherein the polymeric binder includes a functionality selected from the group consisting of anhydride, hydroxyl, carbonyl, carboxyl, amine, amide, ether, lactam, lactone, epoxy, ester, sulfate, sulfonate, sulfinate, sulfamate, phosphate, phosphonate, phosphinate, and combinations thereof.

3. The method of claim 2, wherein the polymeric binder includes a functionality selected from the group consisting of anhydride, carbonyl, carboxyl, hydroxyl, amine, amide, ether, ester, and combinations thereof.

4. The method of claim 3, wherein the binder comprises a polyamide.

5. The method of claim 4, wherein the polyamide is a nylon.

6. The method of claim 5, wherein the nylon is selected from the group consisting of nylon 4/6, nylon 6, nylon 6/6, nylon 11 and nylon 6/12.

7. The method of claim 1, wherein the arc-extinguishing compound is selected from the group consisting of melamine, guanidine, guanidine acetate, guanidine carbonate, 1,3 diphenylguanidine, a cyanurate, a melamine cyanurate, hydantoin, allantoin, urea, urea phosphate, benzoguanidine, dithioammelide, ammeline, a cyanuric halide, and combinations thereof.

8. The method of claim 7, wherein the arc-extinguishing compound is selected from the group consisting of melamine, benzoguanidine, dithioammelide, ammeline, a cyanuric halide, and combinations thereof.

9. The method of claim 8, wherein the arc-extinguishing compound is melamine.

10. The method of claim 7, wherein the melamine has a particle size such that at least 90% by weight of the melamine particles have a size less than 200 μm.

11. The method of claim 10, wherein the melamine has a particle size such that at least 90% by weight of the melamine particles have a size less than 100 μm.

12. The method of claim 11, wherein the melamine has a particle size such that at least 90% by weight of the melamine particles have a size less than 50 μm.

13. A method of extinguishing an electrical arc comprising:

encircling a fuse with an extruded sheath or liner, the sheath or liner comprising an effective amount of an arc-extinguishing compound; a polymeric binder for the arc-extinguishing compound; a polymeric binder having a weight average molecular weight of at least 1,000 daltons that binds the arc-extinguishing compound to the polymeric binder; and a compatible plasticizer for said polymeric binder; and positioning the sheath or liner such that if an arc forms within the sheath or liner, the sheath or liner evolves arc-extinguishing gasses, and the arc-extinguishing gases extinguish the arc.

14. The method of claim 13, wherein the polymeric binder includes a functionality selected from the group consisting of anhydride, hydroxyl, carbonyl, carboxyl, amine, amide, ether, lactam, lactone, epoxy, ester, sulfate, sulfonate, sulfinate, sulfamate, phosphate, phosphonate, phosphinate, and combinations thereof.

15. The method of claim 14, wherein the polymeric binder includes a functionality selected from the group consisting of anhydride, carbonyl, carboxyl, hydroxyl, amine, amide, ether, ester, and combinations thereof.

16. The method of claim 15, wherein the binder comprises a polyamide.

17. The method of claim 16, wherein the polyamide is a nylon.

18. The method of claim 17, wherein the nylon is selected from the group consisting of nylon 4/6, nylon 6, nylon 6/6, nylon 11 and nylon 6/12.

19. The method of claim 13, wherein the arc-extinguishing material is selected from the group consisting of melamine, guanidine, guanidine acetate, guanidine carbonate, 1,3 diphenylguanidine, a cyanurate, a melamine cyanurate, hydantoin, allantoin, urea, urea phosphate, benzoguanidine, dithioammelide, ammeline, a cyanuric halide, and combinations thereof.

20. The method of claim 19, wherein the arc-extinguishing compound is selected from the group consisting of melamine, benzoguanidine, dithioammelide, ammeline, a cyanuric halide, and combinations thereof.

21. The method of claim 20, wherein the arc-extinguishing compound is melamine.

22. The method of claim 21, wherein the melamine has a particle size such that at least 90% by weight of the melamine particles have a size less than 200 μm.

23. The method of claim 22, wherein the melamine has a particle size such that at least 90% by weight of the melamine particles have a size less than 100 μm.

24. The method of claim 23, wherein the melamine has a particle size such that at least 90% by weight of the melamine particles have a size less than 50 μm.

25. A method of extinguishing an electrical arc comprising:

encircling a fuse with an extruded sheath or liner, the sheath or liner comprising an effective amount of an arc-extinguishing compound; a polymeric binder for the arc-extinguishing compound; and a copolymer coupling agent that binds the arc-extinguishing compound to the polymeric binder and comprises a polyolefin that contains reactive anhydride functional groups; and positioning the sheath or liner such that if an arc forms within the sheath or liner, the sheath or liner evolves arc-extinguishing gasses, and the arc-extinguishing gases extinguish the arc.

26. The method of claim 25, wherein the polymeric binder has a weight average molecular weight of about 250 to about 500,000 daltons.

27. The method of claim 26, wherein the polymeric binder has a weight average molecular weight of about 1,000 to about 100,000 daltons.

28. The method of claim 27, wherein the polymeric binder has a weight average molecular weight of about 1,000 to about 50,000 daltons.

29. A method of extinguishing an electrical arc comprising:

encircling a fuse with an extruded sheath or liner, the sheath or liner comprising an effective amount of an arc-extinguishing compound; a polymeric binder for the arc-extinguishing compound; and a copolymer coupling agent that binds the arc-extinguishing compound to the polymeric binder comprising a mixture of two olefins selected from the group consisting of ethylene, propylene, styrene, methyl acrylate, ethylacrylate, n-butylacrylate, glycidylmethacrylate, methylmethacrylate, maleic anhydride, acrylonitrile, methacrylic acid and salts thereof; and positioning the sheath or liner such that if an arc forms within the sheath or liner, the sheath or liner evolves arc-extinguishing gasses, and the arc-extinguishing gases extinguish the arc.

30. The method of claim 29, where in the copolymer is a copolymer selected from the group consisting of styrene and maleic anhydride; ethylene and methylacrylic acid; propylene and methylacrylic acid; ethylene and glycidylmethacrylate; propylene and methylmethacrylate; and styrene and acrylonitrile.

31. The method of claim 29, wherein the copolymer comprises a vinyl monomer and about 2% to about 80% of a monomer having anhydride functional groups, based on the total weight of monomers in the coupling agent.

32. A method of extinguishing an electrical arc comprising:

encircling a fuse with an extruded sheath or liner, the sheath or liner comprising an effective amount of an arc-extinguishing compound; a polymeric binder for the arc-extinguishing compound; and a terpolymer coupling agent that binds the arc-extinguishing compound to the polymeric binder comprising a mixture of three olefins selected from the group consisting of ethylene, propylene, styrene, methyl acrylate, ethyl acrylate, n-butylacrylate, glycidylmethacrylate, methylmethacrylate, maleic anhydride, acrylonitrile, methacrylic acid and salts thereof; and positioning the sheath or liner such that if an arc forms within the sheath or liner, the sheath or liner evolves arc-extinguishing gasses, and the arc-extinguishing gases extinguish the arc.

33. The method of claim 32, where in the terpolymer is a terpolymer selected from the group consisting of ethylene, ethyl acrylate, and maleic anhydride; propylene, ethyl acrylate, and maleic anhydride; ethylene, ethyl acrylate, and glycidylmethacrylate; propylene, ethylacrylate, and glycidylmethacrylate; ethylene, n-butyl acrylate, and maleic anhydride; and propylene, n-butyl acrylate, and maleic anhydride.

34. A method of extinguishing an electrical arc comprising:

encircling a fuse with an extruded sheath or liner, the sheath or liner comprising an effective amount of an arc-extinguishing compound; a polymeric binder for the arc-extinguishing compound; and a coupling agent that binds the arc-extinguishing compound to the polymeric binder in an amount of about 5% to about 100% based on the total weight of the polymeric binder coupling agent mixture and is a selected from the group consisting of a titanate and a zirconate; and positioning the sheath or liner such that if an arc forms within the sheath or liner, the sheath or liner evolves arc-extinguishing gasses, and the arc-extinguishing gases extinguish the arc.

* * * * *